United States Patent [19]

Dahlin

[11] Patent Number: 4,711,132
[45] Date of Patent: Dec. 8, 1987

[54] APPARATUS FOR MASS FLOW RATE AND DENSITY MEASUREMENT

[75] Inventor: Erik B. Dahlin, San Jose, Calif.

[73] Assignee: Exac Corporation, Campbell, Calif.

[21] Appl. No.: 775,739

[22] Filed: Sep. 13, 1985

Related U.S. Application Data

[63] Continuation-in-part of Ser. No. 616,808, Jun. 4, 1984, abandoned and PCT US85/01046 filed Jun. 3, 1985, published as WO85/05677, Dec. 19, 1985.

[51] Int. Cl.$^4$ .............................................. G01F 1/84
[52] U.S. Cl. .................................................. 73/861.38
[58] Field of Search ............... 73/32A, 861.37, 861.38

[56] References Cited

U.S. PATENT DOCUMENTS

| | | |
|---|---|---|
| 2,624,198 | 1/1953 | Pearson . |
| 2,811,854 | 11/1957 | Powers . |
| 2,813,423 | 11/1957 | Altfillisch . |
| 2,821,084 | 1/1958 | Altfillisch . |
| 2,831,349 | 4/1958 | Altfillisch . |
| 2,834,209 | 5/1958 | Jones et al. . |
| 3,132,512 | 5/1964 | Roth . |
| 3,276,257 | 10/1966 | Roth . |
| 3,485,098 | 12/1969 | Sipin ........................... 73/861.38 |
| 4,127,028 | 11/1978 | Cox et al. ..................... 73/861.38 |
| 4,127,028 | 11/1978 | Cox et al. . |
| 4,187,721 | 2/1980 | Smith ........................... 73/861.38 |
| 4,192,184 | 3/1980 | Cox et al. ..................... 73/861.38 |
| 4,252,028 | 2/1981 | Smith et al. .................. 73/861.38 |
| 4,311,054 | 1/1982 | Cox et al. ..................... 73/861.38 |
| 4,422,338 | 12/1983 | Smith et al. .................. 73/861.38 |
| 4,491,025 | 1/1985 | Smith et al. .................. 73/861.38 |

OTHER PUBLICATIONS

Bye, "Mass Flow Measured with Vibration Generators", Fluid Handling; pp. 36–38 (Feb. 1957).
Katys, "Continuous Measurement of Unsteady Flow", Pergamon Press; pp. 45–66 (1964).
Wildhack "Review of Some Methods of Flow Measurement", Science; pp. 191–197 (Aug. 1954).

*Primary Examiner*—Herbert Goldstein
*Attorney, Agent, or Firm*—Claude A. S. Hamrick

[57] ABSTRACT

A Coriolis mass flow rate measuring apparatus including at least one helically configured loop (30) of conduit, a drive mechanism (42) for causing oscillatory movement of a portion of the loop in a direction normal to the direction of flow through the conduit portion and generally parallel to the central axis of the loop, and one or more detectors (46), (48), (56) for detecting the motion resulting from the Coriolis forces exerted on other portions of the loop as a result of the mass flow therethrough and the oscillatory translation thereof. A strain gage (208) and associated processing electronics are also used in combination with the mass flow rate information to determine the density of the flow.

20 Claims, 18 Drawing Figures

U.S. Patent   Dec. 8, 1987   Sheet 1 of 6   4,711,132
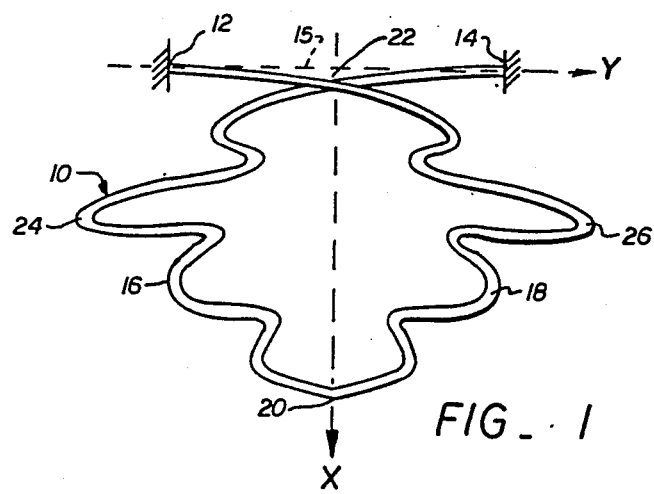
FIG_1
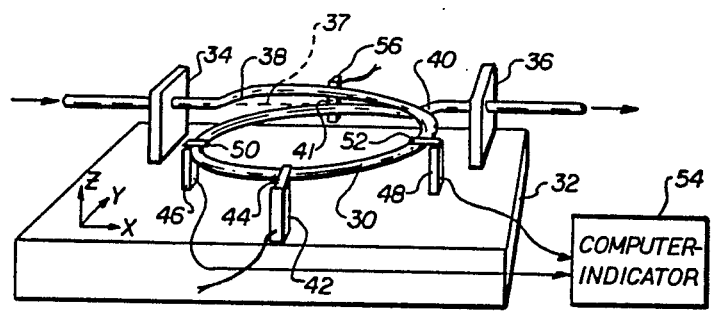
FIG_2
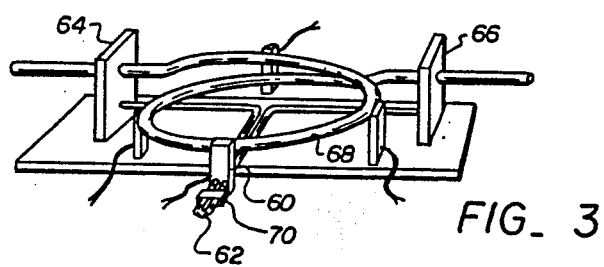
FIG_3

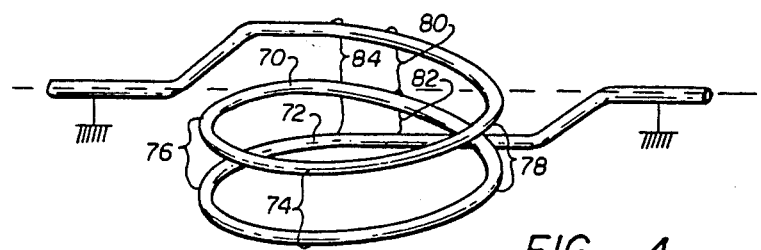
FIG_ 4
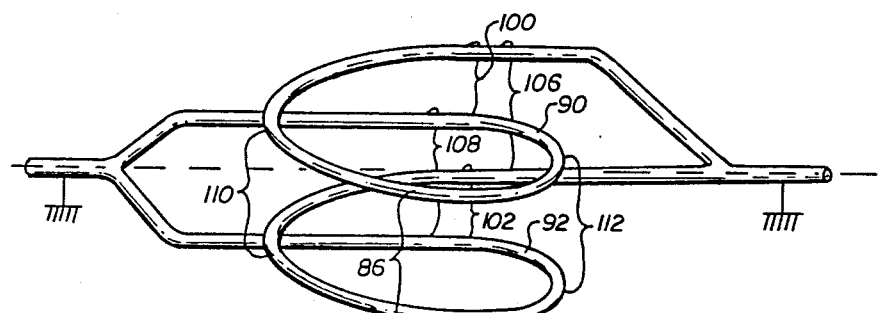
FIG_ 5
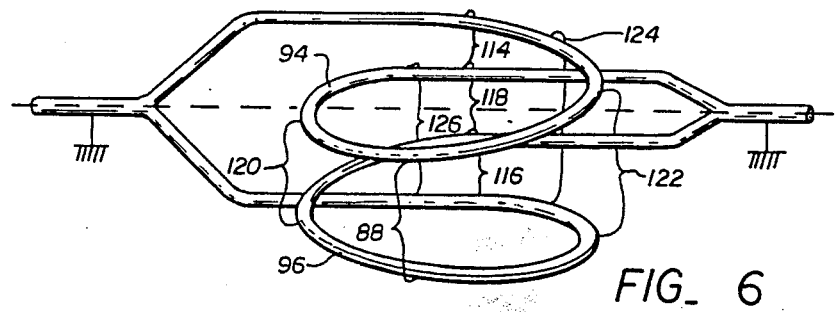
FIG_ 6

APPARATUS FOR MASS FLOW RATE AND DENSITY MEASUREMENT

This application is a continuation-in-part of my earlier filed U.S. patent application entitled "*Apparatus for Mass Flow Rate and Density Measurement*", Ser. No. 616,808, filed June 4, 1984, now abandoned, and PCT Application No. PCT/US85/01046 filed June 3, 1985 and assigned to the Assignee of the present invention.

BACKGROUND OF THE INVENTION

1. Field of the Invention

The present invention relates generally to mass flow rate and density measuring apparatus and more particularly to an improved means for measuring the mass flow rate of a flowing mass using the effects of Coriolis forces and centrifugal forces upon an oscillatorially translated or deflected portion of one or more loops of conduit through which the mass flow is caused to pass.

2. Description of the Prior Art

There has been a continuing need for more accurate and more efficient devices for determining the mass flow rate and density of fluids and flowing solids passed through pipe lines and other various types of conduit. Prior art flow meters of the type including the present invention have in the past been embodied as gyroscopic mass flow meters or Coriolis type mass flow meters and the like.

One such device which utilizes Coriolis forces to measure mass flow is disclosed in U.S. Pat. No. 4,109,524 entitled "Method and Apparatus for Mass Flow Rate Measurement", issued Aug. 29, 1978 to James E. Smith. In this patent an apparatus is disclosed wherein a mechanically reciprocating force is applied to first and second sections of a straight conduit by means of a beam that is disposed parallel to the first and second sections and has its ends mechanically linked to the adjacent ends of the two conduit sections. The adjacent ends of the first and second conduit sections are connected together by means of a short segment of conduit and flexible couplings and the opposite ends of each conduit section is separately supported in cantilever fashion relative to a base structure. The reciprocating forces applied to the conduit are resisted by separate Coriolis forces developed in the first and second conduit sections which act in opposite directions and induce a force moment about the center of the beam which is measured by a torque sensor. By measuring the force moment induced in the conduits (and transferred to the beam) by the Coriolis reactant forces, measurement of the mass flow through the conduit may be made. However, the measurement is complicated because of the need to avoid spurious measurements of the forces resulting from seismic or other vibrational forces transmitted through the support structure. Other similar devices are disclosed in the U.S. patents to Wiley et al, U.S. Pat. Nos. 3,080,750; Sipin, 3,218,851; Souriau, 3,396,579; and Sipin 3,329,019.

Rather than use linear sections of conduit that are pivoted at opposite ends and reciprocated at the adjacent ends, a U-tube or similar configuration is more commonly employed in mass flow measurement. In such cases, the inlet and outlet ends of the legs of the U-shaped tube are fixedly mounted to a base and the bight end of the U-tube is reciprocated. The differential displacement of corresponding portions of the U-tube side legs caused by Coriolis influence on the flow is then measured as an indicator of mass flow rate. Such a technique and apparatus is suggested in the above-mentioned Smith patent and is illustrated in U.S. Pat. No. 4,187,721 for "Method and Structure for Flow Measurement" issued Feb. 12, 1980 to James E. Smith, now U.S. Pat. No. Re. 31,450. As disclosed in the referenced patent, a U-shaped conduit is mounted in a cantilevered manner at the leg ends thereof, and an oscillating means is mounted on a spring arm having a natural frequency substantially equal to that of the U-shaped conduit and is used to provide up and down motion to the center of the bight end thereof. Measuring sensors (flags and photodetectors) are provided which detect the leading and trailing portions of the legs of the U-shaped conduit as they pass through a plane defined by the U-shaped conduit at substantially the mid-point of its oscillation. The time differential of passage of the legs through the midplane is measured as an indication of mass flow rate. Essentially, the same structure is used in the subsequent Smith U.S. Pat. No. 4,422,338 referenced below except that in the latter, a pair of velocity sensors are substituted for the photodetectors, and conditioning electronics are provided for developing signals corresponding to the passage of the side legs through the midplane.

In U.S. Pat. No. 4,127,028 entitled "Coriolis Mass Flow Rate Metering Means" issued Nov. 28, 1978 to Bruce M. Cox, et al, a pair of vibrating generally U-shaped tubes are fixedly mounted at the inlet and outlet ends thereof, in parallelly disposed, spaced apart cantilevered fashion so that the bight ends of the respective tubes are free to move relative to each other. An oscillatory drive mechanism is connected between the bight ends of the respective tubes and actuated to provide opposing reciprocation thereof such that the U-shape members act as the tines of a tuning fork. The frequency of the oscillation of the tubes is adjusted until the tubes vibrate a fixed displacement when a known material is flowing therethrough. The power needed to vibrate the tubes the known displacement at a fixed frequency determines the density of an unknown fluent material flowing the U-shaped tubes. Mass flow rate is detected by photodetectors positioned to operate in the same manner as taught by Smith for a single tube embodiment. Cox also suggests that strain gages or velocity sensors could be substituted for the photodetectors, and acknowledges that it is known in the prior art that there will be a phase shift between the outputs of the two sensors which is proportional to the Coriolis force couple.

The principle teaching of this reference is the narrowing of the separation of the legs of each U-shaped tube proximate the support ends thereof so as to improve the freedom of torsional twist that may be imposed upon the respective tubes by the Coriolis reactance forces. This reference also illustrates a looped tube configuration in FIG. 5 thereof, but fails to teach or suggest how such configuration might be used to provide enhanced flow measurement. It is therefore not believed to anticipate the present invention.

Other prior art known to the present inventor may be found in the U.S. Pat. Nos. to Barnaby et al, 2,752,173; Roth 2,865,201 and 3,049,919; Sipin, 3,355,944; Sipin 3,485,098; Catherall 3,955,401; and Shiota 4,381,680, and the EPO application of Smith, Publication No. EP 0 083 144 A1 which corresponds to U.S. Pat. No. 4,422,338. A listing of prior art utilizing the Coriolis principle may be found in the above-referenced Sipin U.S. Pat. No. Re. 31,450.

A disadvantage of the Smith and Cox type of flow measuring devices, as well as those of others in the prior art, is that they are highly sensitive to to external vibrations which cause the measuring tube or tubes to be subjected to twisting forces other than those imparted by Coriolis reaction forces, and such forces interfere with the accurate measurement of mass flow.

Another disadvantage pertaining to the preferred embodiments in the Smith Reissue U.S. Pat. No. Re. 31,450 and Smith U.S. Pat. No. 4,422,338 is that the proposed methods of time differential measurement at the midplane of the U-tube will produce flow measurement errors when the fluid density is changing.

Yet another disadvantage of the prior art Coriolis type devices is that they are not capable of providing accurate flow data over a wide range of flow due to limitations in sensitivity in the flow structure used.

Still another disadvantage of the prior art devices is that they are not provided with dynamic damping means to reduce the sensitivity to external vibrations.

Yet another disadvantage of the prior art Coriolis type devices is that they utilize a directly proportional relationship between mass flow rate and differential phase angle or differential time measurements.

A still further disadvantage of the prior art Coriolis type devices is that they have substantial errors in mass flow rate if the temperature of the sensing structure changes.

Still another disadvantage of the prior art described in the Smith U.S. Pat. No. Re. 31,450 and U.S. Pat. No. 4,422,338 and Cox, Gonzales U.S. Pat. No. 4,127,028 is that the oscillatory drive motion creates significant bending stress especially at the points where the U-tubes are attached leading to significant danger of stress corrosion. In accordance with the present invention, the drive motion causes primarily torsional stresses absorbed over a certain distance, such as 38 in FIG. 2, resulting in much lower danger to stress corrosion thereby enhancing safety.

Still another disadvantage of the prior art shown in the above patents is that they introduce at least two sharp 90 degree bends in the flow patterns, leading to high pressure drop. The present invention uses loops which have a gradual curvature or circle which gives lower pressure drop.

SUMMARY OF THE PRESENT INVENTION

It is therefore a primary objective of the present invention to provide a new and improved apparatus of the Coriolis type for measuring the mass flow rate of a fluid or fluent solids, or mixtures of these passing through a conduit.

It is another object of the present invention to provide a new an improved apparatus for measuring the density of a mass flowing through a conduit.

A further object of the present invention is to provide means for measuring mass flow rate and density of a mass flowing through a conduit without introducing perturbing objects or mechanisms into the fluid flow path.

Briefly, a preferred embodiment of the present invention includes at least one helically configured loop of conduit, means for causing oscillatory movement of a portion of the loop in a direction nearly normal to the direction of flow through the conduit portion and generally parallel to the central axis of the loop, and means for detecting the result of the Coriolis forces exerted on other portions of the loop as a result of the mass flow therethrough and the oscillatory translation thereof. A strain gage and associated processing electronics are also used in combination with the mass flow rate information to determine the density of the flow.

An important advantage of the present invention is that it enables true mass flow measurement to be made independent of variations of the physical properties of the material flowing through the measuring apparatus.

These and other advantages of the present invention will no doubt become apparent to those skilled in the art after having read the following detailed description of the perferred embodiments illustrated in the several figures of the drawings.

IN THE DRAWINGS

FIG. 1 is a schematic diagram used to illustrate theoretical operation of the present invention;

FIG. 2 is a diagram schematically illustrating a simplified embodiment of one form of the present invention;

FIG. 3 is a diagram schematically illustrating a first alternative embodiment of the present invention;

FIG. 4 is a diagram schematically illustrating a multi-loop embodiment in accordance with the present invention;

FIGS. 5 and 6 illustrate parallel flow multi-looped embodiments of the present invention;

Figure 11:
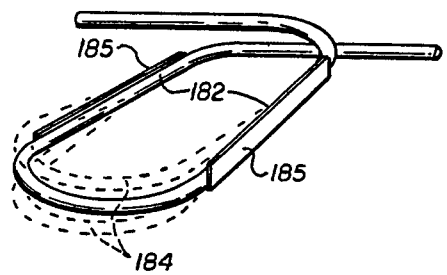
Figure 12:
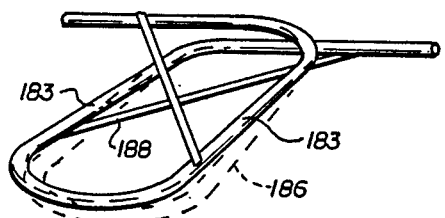
Figure 13:
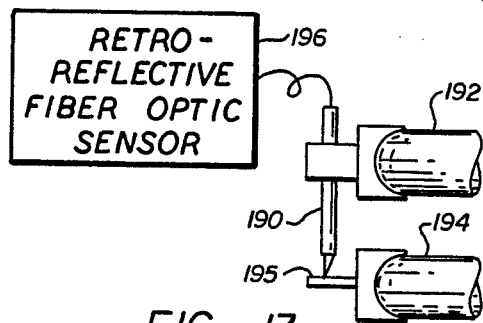
Figure 14:
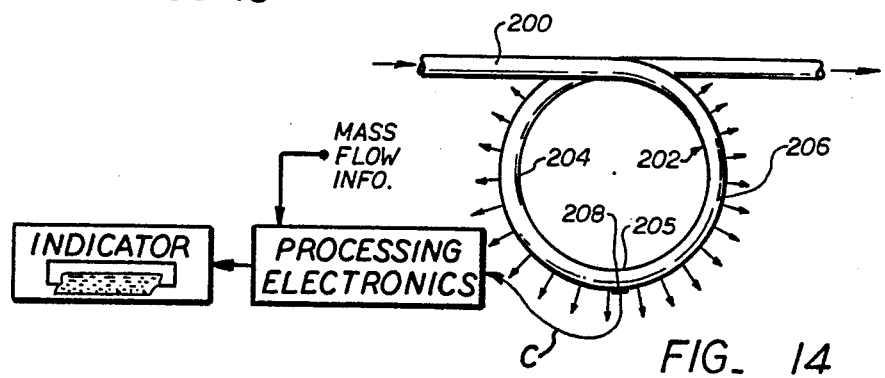
Figure 15:
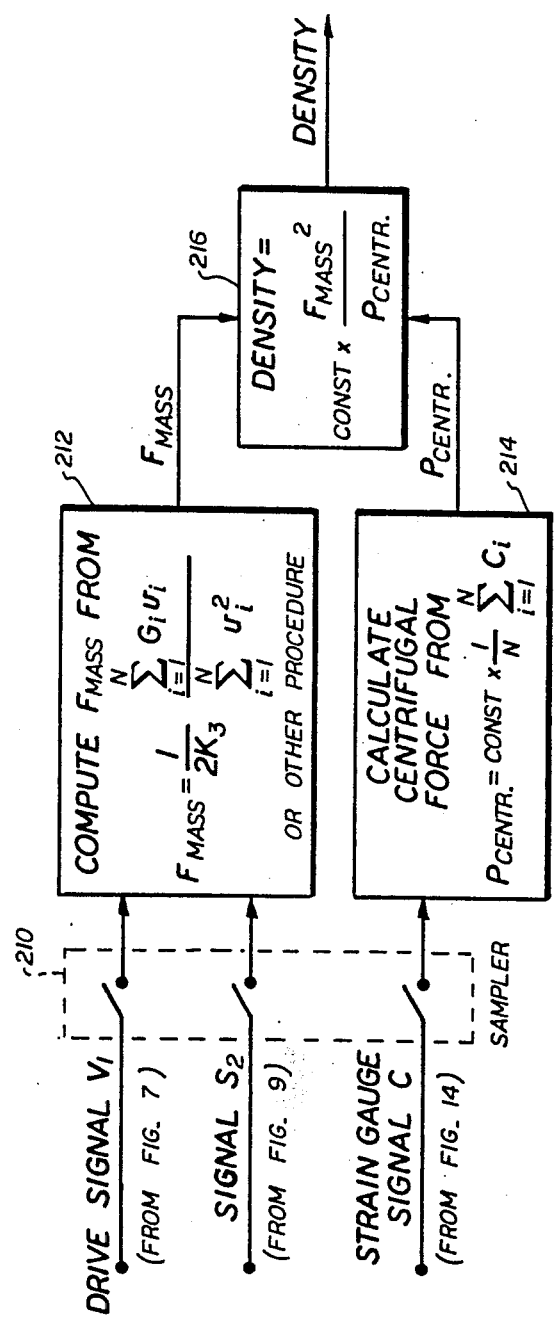

FIGS. 10(a)–10(d) are a set of waveforms illustrating operation of the present invention;

. FIG. 11 is a diagram schematically illustrating an alternative embodiment of the present invention modified to allow increased sensitivity to measurement;

FIG. 12 illustrates a further alternative embodiment of the present invention modified to have increased sensitivity to measurement and reduced sensitivity to outside vibrations;

FIG. 13 illustrates an alternative method of detecting the result of the Coriolis forces in accordance with the present invention;

FIG. 14 illustrates an embodiment including a strain gage and electronic processing apparatus in accordance with the present invention; and FIG. 15 is a block diagram illustrating computational algorithms used in accordance with the present invention.

GENERAL THEORY OF OPERATION

The present invention is based upon the principle that a mass flowing through a looped tube or other straight or curved conduit and experiencing a velocity gradient transverse to the flow path will interact with the wall of the conduit with a force directly related to the transverse velocity gradient and the mass flow rate. When the velocity gradient is caused by the transverse motion of the loop or rotation of the loop about an axis other than the central axis of the loop, the reaction is known as a Coriolis force. The magnitude and direction of the reaction force depends upon the magnitude and direction of the transverse velocity change and the magnitude and direction of the mass flow. If two portions of the loop have the same transverse velocity gradient but have opposite directions of flow, a force couple consisting of equal and opposite reaction forces will result. In accordance with the present invention the result of this force couple is measured as a means of determining the mass flow rate through the conduit.

Referring now to FIG. 1 of the drawings, for purposes of illustration there is shown an example of a generalized helical loop of conduit 10, with its crossed ends mounted to a base structure 12 and 14. The following general theory of the present invention applies for any shape of helical structure and any shape of tube cross-section.

The loop 10 may thus be considered to lie substantially in the X-Y plane for purposes of simplified mathematical analysis; deviation of the tube in the Z direction (normal to the X-Y plane) required to permit crossover is ignored.

Accordingly, for a flow tube that is essentially symmetric in the X-Y plane and around the X-axis, the mass flow and total Coriolis force, $P_{\frac{1}{2}loop}$ acting upon each half section 16 and 18 respectively, is given by the expression $$P_{\frac{1}{2}loop} = F_{mass} v_D \qquad (1)$$

where $v_D$ is the velocity in the Z direction (normal to the X-Y plane) at the drive-point of the loop, such as point 20 in FIG. 1, and $F_{mass}$ is the fluid mass flow.

This equation can be used with another equation to be presented below to describe the dynamics of a loop with the following approximations; namely, (1) the Coriolis forces are assumed to be lumped at a single point for each half loop "center of action point" instead of being distributed with varying magnitude along the tube, (2) the mass of fluid and tube material are assumed to be lumped in a single mass point for each half-loop instead of being distributed along the half-loop, and (3) the motion which is different for the different points on the loop is represented by the motion of the two respective mass points.

At the "center of action point" of the Coriolis force, each half-loop has a certain "participating mass". The center of action is the point where the resultant force of the distributed force for a half-loop is applied and can be computed from the particular tube geometry and the general Coriolis force formula for individual mass elements. "Participating mass" is approximately the weight of the tubing and the fluid in each half-loop but ignores the section between the X-axis and the suspension point. This concept takes into account that the motion is not uniform for different points on the half-loop. The participating mass can be experimentally determined by measuring the natural frequency of the bending mode of oscillation around the X-axis and by comparing it with the theoretical natural frequency of the differential equation to be presented. The participating mass is determined so that the two natural frequencies agree.

The differential equation describing inertial force, damping force and spring action force is:

$$M_p \frac{d^2(Z - Z_D)}{dt^2} + A \frac{d(Z - Z_D)}{dt} + B(Z - Z_D) = P_{\frac{1}{2}loop} \qquad (2)$$

where

A is the damping factor including both natural damping in the material and damping introduced by a damping coil as described hereinbelow;

B is the spring factor describing the restoring force from the spring action due to fixed attachment of the ends of the tube 10;

$M_p$ is the participating mass for one half of the loop;

t is time;

$Z_D$ is the motion of the center of action point due to drive motion alone; and Z is the motion due to drive motion and Coriolis force at the center of action point.

The natural frequency of equation (1) above expressed in radians/unit time is $$W_{th} = \sqrt{\frac{B}{M_p}} \qquad (3)$$

The mode of natural oscillation related to equations 2 and 3 will be referred to as the "Coriolis mode".

The spring factor B can be determined by static application of a force couple at the center of action points (working in opposite directions approximately at the points 24 and 26 of the two sides of the loop 10) in the Z direction, and measuring the deflection of the center of action points.

If the loop 10 is excited at point 20 by an oscillatory force in the Z direction which varies sinusoidally with an angular frequency of w, the Coriolis force $P_{\frac{1}{2}}$ (at constant flow rate) will be a sinusoidal signal having the same frequency. Equation (1) above determines approximately the magnitude of the Coriolis force where $v_D$ has a sinusoidal time variation.

The phase shift between $P_{\frac{1}{2}}$ and $(Z - Z_D)$ in accordance with equation (2) is well understood as published in the literature. For example see Grabbe, Ramo, Woodridge, "Handbook of Automation Computation and Control" volume 1, pages 20-59. Defining the damping coefficient z as $$z = (\frac{1}{2} W_{th})(A/M_p), \qquad (4)$$

if, for example, the drive frequency W is chosen as 0.5 times the natural frequency, $W_{th}$, and the damping coefficient z is chosen as 0.01, then using equations (2) and (3) above, the phase shift can be found to be about −0.8 degrees.

In this example, from equation (4) it can be determined that the ratio of damping factor A to mass $M_p$ is $$\frac{A}{M_p} = 0.02 \; W_{th} \qquad (5)$$

The amount of damping in this example results from the application of a certain amount of damping force to the loop as will be explained further below. With a different amount of damping, or a different selection of drive frequency w, but the same natural frequency in the Coriolis mode, a different amount of phase shift would occur.

If the fluid density changes, the natrual frequency of the Coriolis mode will change and the phase shift at the drive frequency will also change somewhat. For normal density changes of a fluid and for the purpose of calculating an approximate phase shift for a given fluid, and for implementing an approximate compensation for the phase shift by a particular circuit to be described, the density change can be ignored.

A method of compensating for the phase shift between the Coriolis force couple and the structural position in a single or multi-loop embodiment will be described. It is especially useful for digital signal analysis of the waveforms such as described herein. It is also applicable for different embodiments of the motion sensing devices as presented herein. The structural deflection g, where g is proportional to the magnitude of the Coriolis force couple with a factor predetermined by weighing. A linear combination of the time derivative $\dot{g}$ of g, and the integral of the same variable $\dot{g}$ (for example, performed by an analog integration as will be shown below) may be designated G where $$G = K_1 \ddot{g} + K_2 \int \dot{g} dt \quad (6)$$
$$= K_1 \ddot{g} + K_2 g$$

where $\ddot{g}$ is a symbol defined by $$\ddot{g} = d\dot{g}/dt \quad (7)$$

After Laplace transformation G may be expressed as $$G(s) = K_1 s g(s) + K_2 g(s) \quad (8)$$

By selection of the ratio $K_1/K_2$, an arbitrary positive phase shift between 0 degrees and 90 degrees can be introduced relating the new function G to the measurement of $\dot{g}$. This ratio is selected so that it creates a positive phase shift equal to the negative phase shift resulting from the inertia of movement as approximately described by the differential equation (2). By the proper selection of $K_1/K_2$ there will be no significant phase shift between the computed variable G and the drive point velocity $v_D$ in equation (1) as long as the drive velocity is approximately a sinusoidal function. However, some deviation from a single sinewave (harmonic free) waveform is permissible; for example, as caused by disturbing mechanical vibrations. Indeed, the insensitivity to this type of disturbance is a strong advantage of the present invention.

In performing signal analysis, the variable G and the velocity of the drive point $v_D$ are sampled periodically. The rate would typically be 20 times for each full cycle of application of the drive force. However, in the presence of high frequency disturbing vibration of strong magnitude, a much higher frequency would be more suitable. A lower sampling rate speeds up the signal analysis and may be desirable if the flow meter is used for fast acting flow control.

The samples for G and $v_D$ are called $G_i$ and $v_i$ respectively where $i=1,2,3 \ldots N$, and N is the number of sample pairs used for each measurement. The static relationship between a static force couple acting as the Coriolis force couple and the static structure measurement "g stat" is $$g\,stat = K_3 P_{\frac{1}{4}}\,loop\text{-static} \quad (9)$$

For dynamic Coriolis forces, using equation (6) the function G describing dynamic changes may be expressed as $$G = K_1' K_3 \ddot{g} + K_2' K_3 g \quad (10)$$

where $K_1' K_3 = k_1$ and $K_2' K_3 = K_2$ in equation (6).

For simplicity, it may be assumed that $K_2$ is selected as equal to $1/K_3$ and $$G = g + (K_1'/K_2') \ddot{g} \quad (11)$$

This expression illustrates that G is essentially the differential position, velocity or accelleration measurement modified by a derivative term to correct for the phase lag defined by equation (2) above.

Since the variables $P_{\frac{1}{4}\,loop}$ and G are approximately in phase due to the compensation defined by equation (11), one can for a dynamic system use the equation $$P_{\frac{1}{4}\,loop} = (1/K_3) G \quad (12)$$

Similar to equation (9), using this expression in equation (1) and solving for G one obtains $$G = 2K_3 F_{mass} v_D \quad (13)$$

where G and $v_D$ are nearly in phase. In a digital system the variables G and $v_D$ are sampled and the sampled pair, i, is called $G_i$ and $v_i$.

Defining $$\alpha = 2K_3 F_{mass} \quad (14)$$

we then have from equation (13)

$$G = \alpha v_D \quad (14a)$$

$\alpha$ may then be determined by linear regression analysis of sample population $G_i$ and $v_i$. The solution to this expression is for one of the two regression lines related to equation (14a).

$$\alpha^{(1)} = \left( \sum_{i=1}^{N} G_i v_i \right) / \left( \sum_{i=1}^{N} v_i^2 \right) \quad (15)$$

One can also use the other regression line which is defined by $$1/\alpha^{(2)} = \left( \sum_{i=1}^{N} G_i v_i \right) / \left( \sum_{i=1}^{N} G_i^2 \right) \quad (16)$$

The line which divides the angle between the two regression lines in half is given by $$\alpha^{(avg)} = \tan\left[\tfrac{1}{2}(\arctan\alpha^{(1)} + \arctan\alpha^{(2)})\right] \quad (17)$$

and the estimate of the mass flow from this line is obtained from equation (14) as $$F_{mass} = (\tfrac{1}{2} K_3) \alpha^{(avg)} \quad (18)$$

One may, of course, use either one of the regression lines instead of the middle line. An illustration of $F_{mass}$ computed using equations (14) and (15) is given below.

DETAILED DESCRIPTION OF THE PREFERRED EMBODIMENTS

Referring now to FIG. 2 of the drawing, a simplified embodiment of the present invention is illustrated. In this embodiment a circular loop 30 of conduit is mounted to a base 32 by means of two standards 34 and 36. Note that loop 30 is deformed upwardly away from the pipe line axis 37 at 38 and downwardly at 40 to provide clearance at the cross-over point 41. Alternatively, the pipe line matching deformations could have taken place outside the standards 34 and 36.

Opposite cross-over point 41 a loop actuating mechanism 42 is mounted to base 32 and has its force applying armature, or the like, electromagnetically coupled to loop 30 at 44. Actuating means 42 is of any suitable type which is capable of causing reciprocating motion of the engaged loop portion along the Z-axis as defined in equation (2) above.

Disposed on each side of the loop 30 are position sensors 46 and 48 which simultaneously detect the motion (position, or any time derivative on time integral thereof such as velocity or acceleration) of the loop points 50 and 52 relative to base 32 and communicate such measurement to a suitable computing circuit and indicator means 54 which will provide a measurement of the resulting motion caused by the Coriolis forces and thus the mass flow through loop 30. A suitable circuit would be one which in the first step calculated the difference between the properly weighted signals produced by 46 and 48. The weighing factors can be determined so that the difference is zero at zero flow. Alternatively, indicator 54 could be coupled to a suitable means 56 coupled to the crossing portions of loop 30 at the cross-over point 41 and operative to output a signal indicative of the loop separation relative velocity or relative acceleration; such signal also serving to cause indicator 54 to indicate the mass flow through tube 30.

Although the present invention as illustrated in the embodiment of FIG. 2 is a substantial improvement over other prior art devices, it does have the disadvantage that it requires a rigid base 32 for supporting the standards 34 and 36 as well as the actuating mechanism 42 so as to prevent any vibration in the pipe line from being transmitted to the apparatus in a manner which would influence the measurement obtained thereby. It will be appreciated that in this embodiment, because of the rigid base, any vibrational motion transmitted from the pipe line to the base 32 will likewise be transmitted to the drive mechanism 42 and the loop position detectors 46 and 48. Accordingly, vibrational disturbances will not normally affect the accuracy of the measurement. However, it will also be appreciated that seismic disturbances may cause the suspended loop to move relative to the base and thus affect the accuracy of measurement. But, if the loop detection source is the detector 56, a large degree of isolation against seismic disturbance is afforded due to the fact that seismic motion in the Z direction will be equally applied to the upper and lower loop portions at the cross-over point, and the two will be deflected in the same direction with equal intensity.

In FIG. 3 of the drawing, a modification of the FIG. 2 embodiment is illustrated wherein instead of mounting the drive means directly to the base, the drive means 60 is mounted to a counter balancing structure 62 which is rigidly attached to the standards 64 and 66. In this embodiment the counter balancing arm 62 is configured to have the same natural frequency about its support axis as that of the loop 68, and is further provided with an adjustment slide weight 70 for allowing it to be adjusted to match different densities of the mass expected to flow in loop 68. Accordingly, in this embodiment, even though rigid end mounts are required, the base does not need to be vibration resistant since the drive mechanism 60 is not attached directly to the base. Using this alternative, another possible source of error is also avoided in that vibrations generated by the flow meter drive 60 are effectively prevented from influencing the attached pipe line which might reflect energy back into the subject apparatus.

A feature of the present invention that should be noted from the embodiments of FIGS. 2 and 3 is that stresses induced in the tube at its attachment points to standards 34(64) and 36(66) due to actuation by the drive means 42(60), i.e., drive mode stresses, are primarily torsional rather than bending. On the other hand, stresses at such points caused by Coriolis forces, i.e., Coriolis mode stresses, are primarily bending in nature.

In order to increase the sensitivity of the present invention to Coriolis forces, serial and parallel combinations of cross-over loops, such as are illustrated in FIGS. 4–6 of the drawing, may be utilized. In the case of the serial double-cross-over loop of FIG. 4, a drive force might be applied between the two loops 70 and 72 at 74 causing deflection of the two loops in opposite directions. Means provided at 76 and 78 could detect changes in separation, i.e., relative position, velocity or acceleration between the loops, with the dynamic difference in separation being used for computation of the mass flow rate. Alternatively, detection of the loop separations at 80 and 82, or the difference therebetween, could be used as mass flow rate indicators. Similarly, detection of separation between the loops at 84 could likewise be utilized.

It will of course also be appreciated that the relative positions of corresponding portions of the individual loop above a base or other reference could also be detected as depicted in FIG. 2 of the drawings, and the differences therebetween used to determine mass flow rate. The serial double-cross-over loop (FIG. 4) has excellent flow sensitivity and is especially suited for measuring low flor rates. However, the structure is somewhat sensitive to outside vibrations and requires the use of damping schemes, as will be described below.

In the parallel loop embodiment illustrated in FIG. 5, both loops are wound spirally in the same direction, while in the FIG. 6 embodiment, the upper loop is wound spirally advancing downwardly while the lower loop is wound spirally advancing upwardly. With actuating forces applied between the loops at 86 in FIG. 5, and 88 in FIG. 6, in addition to the loop separation differential measurements (position, velocity, accelleration or other time derivatives or integrals) discussed relative to the FIG. 2 embodiment, measurements could be taken of the top gap 100 (114 in FIG. 6) or the bottom gap 102 (116), or the difference between the top gap 100 (114) and bottom gap 102 (116) could be measured. Similarly, the differential loop characteristics of separation at 108 (118), 110 (120), 112 (122), could be taken as indicators, as could the differences between 110 and 112, (120 and 122). Measuring the position difference, or velocity of relative motion or acceleration between the upper and lower loops on opposite sides of the loops, and then calculating the differences between these distances (or velocities or accelerations) is the measurement mode which is believed to be the most sensitive to mass flow.

As an alternative embodiment of difference measurement, the difference in phase angle $\Delta\theta$ measured at a given signal level for the position, velocity or acceleration signals produced by sensors 46 and 48 in FIG. 2 can be used. If velocity sensors are used, $F_{mass}$ would be calculated by computational electronics from the equation $$F_{mass} = \frac{\tan\frac{\Delta\theta}{2}}{2KRw_D\left(\sin\phi - \cos\phi\tan\frac{\Delta\theta}{2}\right)} \quad (19)$$

where $\Delta\theta$ in the phase angle difference between the outputs of the two velocity sensors, $$\phi = \frac{\pi}{2} - \arctan\left(\frac{2z_c w_D}{w_c^2 - w_D^2}\right), \quad (20)$$

$$R = \frac{w_c^2}{\sqrt{(w_c^2 - w_D^2)^2 + 4z_c^2 w_D^2}}$$

K = a loop "flexibility constant" defining the change in loop position at one of the velocity sensor locations per unit Coriolis force on the corresponding half-loop.

$w_c$ is the actual natural frequency of the mode excited by the Coriolis forces (the Coriolis mode) and corresponds to the theoretical value $W_{th}$ in equation (3); and $z_c$ is the actual damping coefficient for the Coriolis mode (corresponds to the theoretical value z in equation (4)).

Note that the phase angle difference $\Delta\theta$ is equal to the drive frequency $w_D$ times the time difference between the waveforms developed by the detectors operating at left and right positions such as 46 and 48 respectively in FIG. 2, 76 and 78 in FIG. 4, or 110 and 112 in FIG. 5. See *Electronic and Radio Engineering* by Frederick E. Terman, McGraw-Hill (1955).

It should also be noted that the constant K depends on the temperature as well as material and geometrical dimensions of the loop because in most materials the elasticity (or Young's) modulus is varying with temperature. As a special embodiment, one can, during flowmeter usage in a process, measure the temperature of the tubular wall and input the value of this variable into a computing circuit or digital computer and calculate the current value of K. The change in Young's modulus with temperature is tabulated in literature or can be determined experimentally. The value of K at a given reference temperature is determined by calibration for each flowmeter design or each individual unit.

Equation (19) is different from and more accurated than the equations presented and implemented in the prior art.

Using differential phase angle and drive frequency measurement, it is desirable to drive the device at its resonant frequency because the waveform developed by detectors responding to Coriolis forces will be free of harmonics. Using position or accelleration sensors one can easily derive similar formulas, Well known prior art apparatus capable of detecting the phase angle differences is disclosed in *Applications Handbook of Precision Phase Measurement* (1975) by Dranetz Engineering Laboratories, Inc. of South Plainfield, N.J., and *Hewlett-Packard Application Note* 200-3 (1974) entitled "Precision Time Interval Measurement Using an Electronic Counter"

Figure 7:
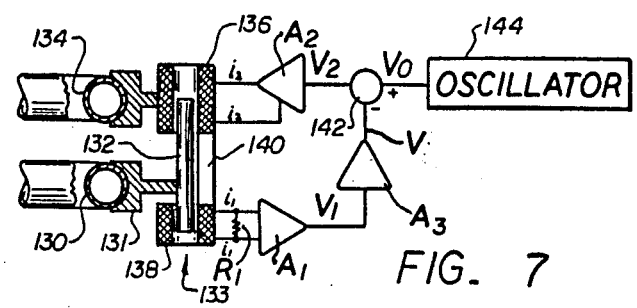
FIG. 7 is a diagram schematically illustrating one method of applying oscillatory energy to the loop or loops in accordance with the present invention.

Turning now to FIG. 7 of the drawing, one possible implementation of a drive system of the type depicted at 42 in FIG. 2 is illustrated in detail. Mounted to one tube 130 by means of a standoff 131 is a permanent magnet 132. Attached to the loop directly above, as illustrated by the tube segment 134, is a double coil mechanism 133 including an upper winding 136 and a lower winding 138 which are mechanically attached to each other by a member 140, but are electrically isolated from each other. The assembly 133 is mounted relative to magnet 132 such that as current is input to winding 136 a motive force will be applied the magnet which will tend to drive the loop segment 130 relative to the loop segment 132. As the magnet 132 moves within the lower coil 138, a signal will be induced therein which is proportional to the velocity of the magnet with respect to the velocity of the coil as it moves along the axis of the assembly 133. This signal, illustrated as the current $i_1$ is proportional to the velocity difference between the tubes 130 and 134. The voltage created by $i_1$ in the resistor $R_1$ is input to a differential amplifier $A_1$, which in turn will generate a voltage signal $V_1$ that is also proportional to the velocity difference.

The voltage $V_1$ is then fed through an amplifier $A_3$ whose output V is subtracted by an analog computing device 142 from an input voltage $V_0$ generated by an oscillator 144 that generates a suitable periodic voltage signal $V_0$ in a form such as a sine wave. The difference $V_0 - V = V_2$ is then fed into an amplifier $A_2$ that generates a drive current $i_2$ which, on passing through the drive coil 136, produces a magnetic field that creates a magnetic force which acts on permanent magnet 132 causing it to oscillate up and down within the winding 136, thereby causing loop 130 to be moved up and down relative to loop 134.

The purpose of the velocity feedback loop, including winding 138 and amplifier $A_1$, is to control the amplitude of the tube oscillation at a desirable magnitude, even if the oscillator is operated at or near the natural frequency of the tube. Without this velocity feedback, or some other means for applying damping force to the tubes, should the oscillatory frequency be set at the natural frequency of the tubes it would cause the tubes to be driven to their elastic limit and perhaps failure.

The behaviour of the closed feedback loop illustrated in FIG. 7 can be approximately described by the transfer function $$\frac{X}{V_0} = \frac{K_2 K_3}{ms^2 + s[a + KK_1 K_2 K_3 K_4[ + b} \quad (21)$$

where

K = velocity feedback loop gain $(V/V_1)$

Figure 9:
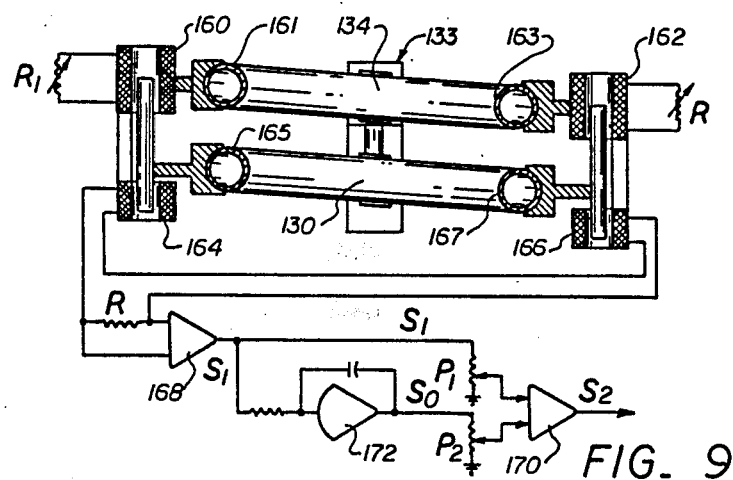
FIG. 9 is a diagram schematically illustrating a method of detecting the Coriolis influence on multiple loops in accordance with the present invention.

X = the separation between the tubes at points 161 and 165 in FIG. 9, $K_1$ is the gain factor $(V_1/i_1)$, $K_2$ is the gain factor $(i_2/V_2)$, $K_3$ is the force between the drive coil 136 FIG. 7 and magnet 132 per unit current $i_2$, $K_4$ is the magnitude of current $i_1$ per unit velocity difference between drive coil 136 and permanent magnet 132, s is the Laplace operator symbol, m is the mass of both tubes 130 and 134 and the fluid contained therein including only the circular portion of the loops, a is the damping constant of the structure for the drive motion, and b is the spring constant of the structure for the drive motion.

The expression $a + KK_1K_2K_3K_4$ shows that the normally small damping constant "a" without the velocity feedback loop has been enhanced. By selection of appropriate gain factors, damping can be chosen to make the drive amplitude and velocity signal $V_1$ follow the oscillation signal $V_0$ in a desirable fashion.

Figure 8:
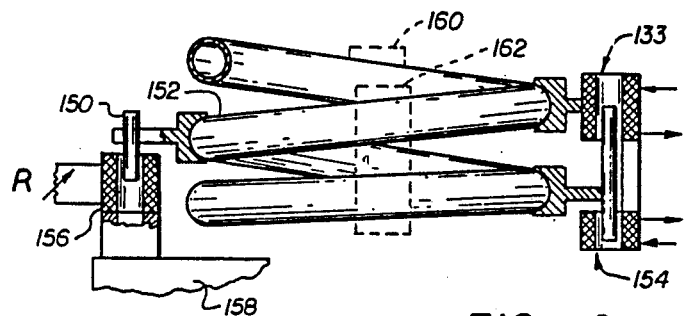
FIG. 8 is a diagram schematically illustrating a damping technique used in accordance with the present invention.

Any flow tube will exhibit a natural mode of vibration with low damping. Artificial damping and control of the drive may of course be achieved as illustrated in FIG. 7. However, to accomplish damping without velocity and amplitude control, a similar system, such as is illustrated in FIG. 8, can also be used. Such a device would be a valuable addition to any type of Coriolis flow sensor, but would be an important improvement over the apparatus shown in the above-referenced Smith patents.

In this embodiment, a permanent magnet 150 is attached to the center loop portion 152 of a double serial loop device that is driven by an actuating assembly 154 such as was previously described at 133 in FIG. 7. The magnet 150 is disposed to move vertically within a damping coil 156 which is rigidly attached to a device base 158. Connected across the winding of coil 156 is a variable load resistor R. The current induced in coil 156 by motion of the magnet 150 therewithin creates a current which passes through resistor R and which is proportional to the velocity of the motion of the magnet relative to coil 156. Energy generated by motion of the magnet within coil 156 will be absorbed by energy dissipated in the resistor R. Accordingly, by selection of coil size, number of turns, permanent magnet strength, and the value of resistor R, the extent of damping achieved by such device can be selected to accomodate a particular application.

As another alternative which is shown in FIG. 9, damping coils 160 and 162 can be physically tied to velocity sense coils 164 and 166 in a double loop serial (FIG. 4) or parallel (FIG. 5 or 6) device configuration. In this particular embodiment, the velocity sense coils 164 and 166 are wound in opposite directions and connected together serially so that when both gaps close at the same rate, the total induced EMF is 0. The output currents developed by coils 164 and 166 in this embodiment are passed through a resistor R to develope a voltage that is fed into a differential amplifier 168 which in turn generates an output signal $S_1$ that is proportional to the velocity difference between the relative motions of tube portions 161 and 165, and 163 and 167 respectively. The amplifiers 170 and 172, and the potentiometers $P_1$ and $P_2$ perform a phase-shifting function to compensate for the phaseshift between the Coriolis and the related motion of the flow tubes as described mathematically by the equations (2)–(8). This compensation is an alternative design feature which is especially useful with digital signal analysis schemes such as described by equations (9)–(18). The signal $S_1$ is fed through the variable potentiometer $P_1$ to generate a proportional voltage that is fed into one side of the difference amplifier 170. Simultaneously, $S_1$ is also fed through the integrator 172 to develop a corresponding position signal $S_0$, and this signal is passed through the second potentiometer $P_2$ to generate a proportional voltage that is fed into the other side of amplifier 170. The resultant output signal $S_2$ generated is described by equation (8) where the coefficients $K_1$ and $K_2$ correspond to the settings of the potentiometers $P_1$ and $P_2$ respectively.

Position information may be obtained in this embodiment by integration of velocity (or double integration of acceleration if such sensors are used), and difference in position can be computed by integration of the velocity difference (or double integration of the acceleration difference) as shown in FIG. 9, velocity data is equivalent to position information for the purpose of measurement. The effect of initial conditions associated with integration disappear quickly since the analysis of amplitude is made during many cycles of periodic excitation of the loop for each point of measurement of mass flow rate.

In the illustrated embodiment, the sense coils 164 and 166 are connected serially so that, as suggested above, in phase motion of the tube portions 164–167 will produce opposing currents in the resistor R, thus resulting in a net voltage drop across R of 0. Under influence of flow through the tubes, induced Coriolis forces in the portions 165 and 167 will cause relative movement of these tube sections in opposite directions, and a net current resulting from the sum of the induced voltages in the sense coils 164 and 166 will be delivered through the resistor R. As indicated above, the voltage developed across resistor R is then fed into the differential amplifier 168 and the output thereof is integrated by 172 to convert the signal $S_1$, which represents the velocity difference between the relative motion between the tubes 161 and 165 and the tubes 163 and 167, to a separation difference signal $S_0$.

Figure 10:
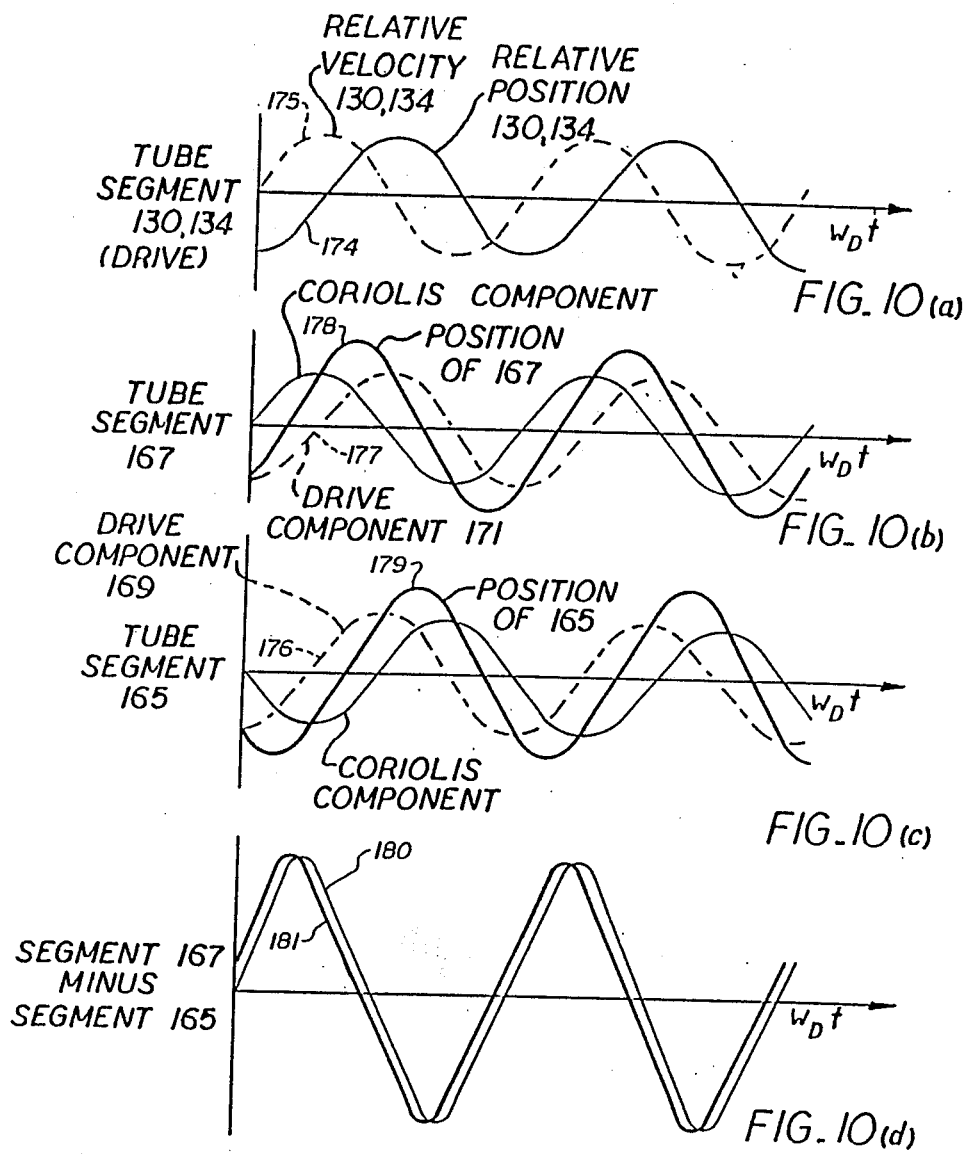

In FIG. 10 the relationship between steady state signals with sinusoidal drive velocity is illustrated. The curves in FIG. 10 represent position and acceleration with reference to the housing or mounting platform, such as 32 in FIG. 2, for description of the motion of a single loop. The same curve shapes apply for characterization of the relative position (distance between) of the loops and the time derivative thereof (relative velocity) for double or multiple loop configurations, such as are shown in FIGS. 4–6. In he latter case, the behavior is independent of the exact position of the loops with respect to the drive component curves 176 in part (c) and 177 in part (b) of FIG. 10. Similarly, it will be appreciated that any Coriolis induced deflection will be nearly inphase with the velocity component of the drive motion, and will be positive with respect to tube segment 167 and negative with respect to tube segment 165. Accordingly, by summing the Coriolis components and the drive components, the Coriolis induced positional displacements of tube segments 167 and 165 can be derived, and such displacements are respectively illustrated in parts (b) and (c) by the indicated waveforms 178 and 179.

In part (d), the difference between the position of curves 165 and 167 is depicted as 180 with no visible phase lag between drive velocity and Coriolis force. In actuality, it will be noted that there is a small phase lag of approximately minus one degree depending upon drive, "Coriolis mode", natural frequency ratio and damping. Curve 181 illustrates this with exaggerated magnitude. Note also that the magnitude of the Coriolis component 178 or 179 is very small compared with the drive components 171 and 176, and that FIG. 10 shows exaggerated size of the Coriolis component for ease of illustration.

For effective signal analysis using digital sampling of the drive velocity and the response to the Coriolis force, it is desirable that these signals be synchronized. By suitable selection of the settings of potentiometers $P_1$ and $P_2$ of the circuit of FIG. 9 appropriate compensation can be made such that the signal $S_2$ is caused to be closely in phase with the drive velocity signal.

In order to increase the sensitivity of the devices heretofore described, one possible modification is to extend the portions of the loop which are subject to Coriolis forces. In FIGS. 11 and 12 such extensions are illustrated wherein the loop sides 182 and 183 are lengthened. However, in so doing two potential problems may be encountered, i.e., "wobble" and "roll". In FIG. 11 the problem of wobble due to bending of the lengthened tube sections in the vertical direction, as illustrated by the dashed lines 184, as the loop is driven. In order to stiffen the sides 182 to avoid the woddle problem, one solution is to attach stiffening plates 185 to each side 182 so that the sides are no longer free to bow.

The second problem that is encountered with such modification, the problem of "rolling", is illustrated in FIG. 12 by the dashed lines 186. In this situation there is a tendency for the loop 182 to deflect the loop laterally, or in effect to "roll" the loop, either leftwardly or rightwardly (parallel to the X-Y plane). In order to eliminate this tendency, roll restraint arms such as those illustrated at 187 and 188 may be utilized. The restraint arms may be in the form of rigid or semi-rigid rods or bars welded directly to the tube at either end. However, these members could also be in the form of flexible cables since the restraint imposed is tensil in nature. It will also be appreciated that a combination of the two solutions shown in FIGS. 11 and 12 might also be utilized to avoid both roll and wobble deformation.

In FIG. 13 an alternative sensing arrangement is illustrated wherein instead of utilizing an electromagnetic sensing means to sense relative motion between adjacent tube segments, or a tube segment and a base, a fiber optic sensor may be utilized. In this case a fiber optic bundle 190 is attached to the upper tube 192 and a reflective plate 195 is attached to the lower tube 194 (or to a base). The fiber optic sensor apparatus 196 then causes a beam of light to pass through a portion of the optical bundle 190, be reflected by the surface 195 and be returned through a different portion of the bundle 190 to the sensor 196 to effect positional detection. It will of course be understood that any other suitable means of detecting relative position or relative velocity or accelleration information may also be used in accordance with the present invention.

The inclusion of density measurement as part of this invention is illustrated in FIG. 14 wherein for simplicity the Coriolis measuring apparatus is not shown. This feature utilizes the fact that the centrifugal forces acting upon each element of the fluid flowing in the looped portion 202 of tube 200 is directed from the center of curvature for the element perpendicular to the tube section the element is in. Since the loop is relatively flat, the centrifugal forces for the elements are not far removed from the plane of the drawing. Thus, the centrifugal force is inversely proportional to the radius of curvature for the element, proportional to the mass within the element and proportional to the square of the fluid velocity. Moreover, the centrifugal forces on the output half 204 of the loop will cause a pull to the left at point 205 and the forces on the input half 206 of the loop will cause a pull to the right at point 205. The opposing forces at 205 will thus cause a strain in the material that is related to the aggregate of the centrifugal forces on the whole test section. Since the Coriolis forces cause no strain at the point 205, measurement of the strain at that point 204 may be accomplished using a simple strain gauge 208. Moreover, a strain gauge measurement taken anywhere along the loop will furnish information permitting the accomplishment of a density measurement in conjunction with the Coriolis mass flow rate measurement although the calibration relationship will be more complex.

For the illustrated configuration, the ratio of the total centrifugal force for the half circle 204 acting in the horizontal direction at the point 205, and the total Coriolis force acting upon the same half circle is directly proportional to the velocity of the material in the fluid and is independent of all other characteristics of the fluid.

The density of the material in the conduit is directly proportional to the square of the measured mass flow rate divided by the centrifugal force acting upon the half-loop. One circuit by which such information may be developed is illustrated in FIG. 15 and includes a means 210 for sampling the drive signal $V_1$ (from FIG. 7) and signal $S_2$ (from FIG. 9), and strain gauge signal C (from FIG. 14), a means 212 for computing the mass flow rate $F_{mass}$ from the sampled signals $V_1$ and $S_1$, a means 214 for calculating the centrifugal force Pcentr. from the strain gauge signal C, and a means 216 for calculating the density from mass flow rate and centrifugal force.

Although the present invention has been described above by referring to several examples illustrated in the drawing, it is to be understood that such embodiments are presented for illustration only and are not intended to in any way be limiting. It is intended that the appended claims be interpreted as covering all embodiments, alterations and modifications as fall within the true spirit and scope of the invention.

What is claimed is:

1. A flow meter for measuring the mass flow rate in a stream of flowing material, comprising:

tubular conduit means arranged to form at least one loop having an entrance portion, an exit portion crossing said entrance portion in spaced apart relationship, an actuated portion, a first detection portion coupling said entrance portion and said actuated portion, and a second detection portion coupling said actuated portion and said exit portion, said conduit means being adapted to receive, conduct and then emit said stream of flowing material and having a natural frequency of oscillation in the Coriolis mode of $w_C$ and a natural frequency of oscillation in the drive mode of $w_D$, where $w_D$ is substantially different from $w_C$;

actuating means for causing said actuated portion to oscillate between positions on opposite sides of a rest position;

damping means coupled to said tubular conduit means for allowing selective adjustment of the damping coefficient thereof;

detection means for detecting motive differences occurring between said entrance portion and said exit portion caused by Coriolis forces induced in said first detection portion of said second detection portion as said actuating means causes said actuated portion to oscillate; and computing and indicator means responsive to said detection means and operative to indicate the mass flow rate of material flowing through said tubular conduit means.

2. A flow meter as recited in claim 1 wherein said detection means includes a first sensor means for detecting the dynamic position of said first detection portion relative to a reference and for generating a first position signal, and second sensor means for detecting the dynamic position of said second detection portion relative to said reference and for generating a second position signal, said computing and indicator means utilizing the difference between said first and second position signals to provide an indication of the mass flow rate of material flowing through said tubular conduit means.

3. A flow meter as recited in claim 2 wherein said first sensor means includes an electromagnetic signal generator having a first magnetic element affixed to said reference and a second magnetic element affixed to said first detection portion, said second element being magnetically coupled to said first element and disposed to move relative thereto.

4. A flow meter as recited in claim 1 wherein said tubular conduit means includes two identical serially connected loops of the type recited in claim 1 wherein the exit portion of one loop is connected to the entrance position of the other loop and wherein said damping means is coupled between the juncture of said first and second loops and said reference.

5. A flow meter as recited in claim 4 wherein said damping means includes an electromagnetic signal generator having a first magnetic component affixed to said reference and a second magnetic component affixed to said juncture, said second component being magnetically coupled to said first component and disposed to move relative thereto, and resistive load means coupled to said first magnetic component and operative to dissipate energy induced therein by relative movement of said second component.

6. A flow meter as recited in claim 1 wherein said tubular conduit means includes two loops of the type recited in claim 1 connected to form parallel flow paths and having corresponding parts disposed in spaced apart parallel relationship, and wherein said actuating means is coupled between the actuated portions of each loop and serves to apply simultaneous equal and oppositely directed actuating forces to each loop.

7. A flow meter as recited in claim 6 wherein said detection means includes a first sensor means coupled between the first detection portion of said first loop and the first detection portion of said second loop, and a second sensor means coupled between the second detection portion of said first loop and the second detection portion of said second loop, said first and second sensors being operative to develope output signals indicative of the motive relationships of the corresponding portions of said first and second loops.

8. A flow meter as recited in claim 7 wherein said first and second sensor means each include a pair of coaxially disposed electromagnetic windings and a permanent magnetic element magnetically coupled to both said windings, said windings being rigidly secured to one of said loops, and said magnetic element being rigidly secured to the other of said loop, and resistive impedance means connected to one winding of each said pair of windings for dissipating energy induced therein by movement of said magnet relative to said windings, and means connecting the other winding of each said pair of windings to said computing and indicator means.

9. A flow meter as recited in claim 7 wherein said first and second sensor means are velocity sensors and said computer and indicator means calculates mass flow rate according to the formula $$F_{mass} = \frac{\tan\frac{\Delta\theta}{2}}{2KRw_D\left(\sin\phi - \cos\phi\tan\frac{\Delta\theta}{2}\right)}$$

where $\Delta\theta$ is the phase angle difference between the output signals developed by said first and second velocity sensor means;

$$\phi = \frac{\pi}{2} - \arctan\left(\frac{2z_C w_D}{w_C^2 - w_D^2}\right);$$

K is a constant, or alternatively, a variable computed from measurement of the flow tube temperature related to Young's modulas;

$$R = \frac{w_C^2}{\sqrt{(w_C^2 - w_D^2)^2 + 4z_C^2 w_D^2}};$$

$W_D$ is the natural frequency of the tubes in the drive mode;

$W_C$ is the actual natural frequency of tubes in the Coriolis mode; and $Z_C$ is the actual damping coefficient for the Coriolis mode.

10. A flow meter as recited in claim 7 wherein the outputs generated by said first and second sensor means are input to a difference amplifier in said computing and indicating means which generates a velocity difference signal that is input to a first input of a second difference amplifier and to an integrator which develops a separation difference signal which is input to a second input of said second difference amplifier, and wherein in response thereto said second difference amplifier develops an output signal corresponding to the net Coriolis force sensed by said detection means.

11. A flow meter as recited in claim 1 wherein said tubular conduit means includes at least first and second loops of the type recited in claim 1 wherein the exit portion of one loop is connected to the entrance portion of the other loop to form a serial flow path for said flowing material.

12. A flow meter as recited in claims 6 or 11 wherein said actuating means includes a pair of coaxially disposed electromagnetic windings connected to one of said loops, and a permanent magnet element magnetically coupled to both said windings and physically connected to the other of said loops, one of said windings having a drive current applied thereto and acting to electromagnetically drive said magnet element and said other loop relative to said one loop, the motion of said magnet element relative to the other of said windings causing a velocity feedback current to be induced in said other winding proportional to the velocity of said other loop relative to said one loop.

13. A flow meter as recited in claim 12 wherein said actuating means further includes a source of periodic voltage, means responsive to said feedback current and operative to develop a feedback voltage, means responsive to said periodic voltage and said feedback voltage and operative to develop a drive voltage, and means responsive to said drive voltage and operative to develop said drive current.

14. A flow meter as recited in claim 1 wherein said tubular conduit means has a pair of elongated leg portions disposed to extend generally parallel with each other and respectively forming said first detection portion and said second detection portion, and further includes stiffener means attached to each said elongated leg portion to prevent it from bowing in the direction normal to a plane generally including said elongated leg portions.

15. A flow meter as recited in claim 1 wherein said tubular conduit means includes a pair of elongated leg portions respectively forming said first detection portion and said second detection portion, and further including a first roll restraint member coupling said entrance portion to one of said elongated leg portions, and a second roll restraint member coupling said exit portion to the other of said elongated leg portions whereby said loop is prevented from deflecting in the plane generally defined by said elongated leg portions.

16. A flow meter as recited in claim 1 and further comprising strain gauge means affixed to said tubular conduit means for developing a strain signal proportional to the centrifical forces developed in said loop by said flowing material, and wherein said indicator means is further responsive to said strain signal and operative to use said strain signal in combination with the indicated mass flow rate to further indicate the density of the mass flowing through said tubular conduit means.

17. A flow meter as recited in claim 1 wherein said detection means detects a characteristic of the change in the spacing between said entrance portion and said exit portion at the crossover point.

18. A flow meter as recited in claim 17 wherein the said motive differences are the differences in arrival times of velocity signals corresponding to the motion of said entrance portion and said exit portion at one or more predetermined reference values.

19. A flow meter as recited in claim 1 wherein the said motive differences are the differences in arrival times of said entrance portion and said exit portion at one or more predetermined reference points of position, velocity or acceleration.

20. A flow meter as recited in claim 1 wherein said detection means detects a characteristic of the change in the spacing between said entrance portions and said exit portions at the crossover point.

* * * * *